Figure 1:
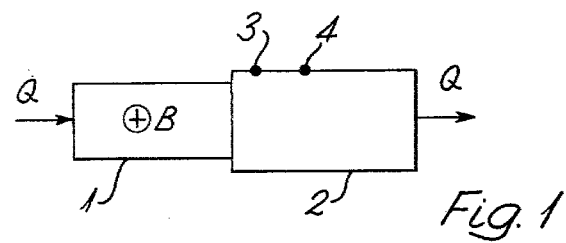

United States Patent [19]
Challis

[11] 4,242,905
[45] Jan. 6, 1981

[54] PHONON SPECTROSCOPY
[75] Inventor: Lawrence J. Challis, Wollaton, England
[73] Assignee: National Research Development Corporation, London, England
[21] Appl. No.: 60,681
[22] Filed: Jul. 25, 1979
[30] Foreign Application Priority Data
  Aug. 10, 1978 [GB] United Kingdom ............... 32932/78
[51] Int. Cl.³ ............................................. G01N 25/00
[52] U.S. Cl. ................................................... 73/15 R
[58] Field of Search .................. 73/15 R, 15 A, 15 B, 73/15 FD

[56] References Cited
PUBLICATIONS
Spectrum, No. 149 (1977), pp. 9–11.
Challis et al., "An Analysis of the Effects of Frequency Crossing in the Resonant Scattering of Thermal Phonons", J. of Physics C., vol. 8 (1975), pp. 1475–1505.

Primary Examiner—Donald O. Woodiel
Attorney, Agent, or Firm—Cushman, Darby & Cushman

[57] ABSTRACT
A versatile method of phonon spectroscopy in which frequency crossing effects are utilized. A heat current is passed through a composite structure incorporating two bodies respectively containing different types of resonant phonon-scattering center. A varying external perturbation, suitably a magnetic field, is applied to the structure so as to affect the resonant frequency for only one of these types. The temperature difference between two points on the structure is monitored as the perturbation varies, this temperature difference exhibiting an excursion when the resonant frequencies for the two types of center coincide.

12 Claims, 3 Drawing Figures

PHONON SPECTROSCOPY

This invention relates to phonon spectroscopy and is concerned in particular with methods in which frequency crossing effects are utilised. By way of background reference may be made to an article published in Spectrum No. 149 (1977) pages 9–11, which gives a brief review of the subject of phonon spectroscopy, and to a series of three papers published in *Journal of Physics C: Solid State Physics*, Vol. 8 (1975) pages 1475–1505, in which frequency crossing effects are discussed in some detail.

In known methods of phonon spectroscopy utilising frequency crossing effects, the properties of resonant phonon-scattering centres in a solid body are investigated by passing through the body a heat current of phonons of broad spectral width while subjecting the body to a varying external perturbation which affects the resonant frequency of at least one scattering process associated with the relevant centres; the external perturbation is commonly a magnetic field, but could instead be an electric field or a mechanical stress. The variation of the external perturbation gives rise to a variation in the thermal conductivity of the solid body, which exhibits a sharp maximum or minimum when a frequency crossing occurs, i.e. when the size of the perturbation is such as to bring into coincidence the resonant frequencies of two scattering processes associated with the relevant centres; the variation in thermal conductivity can conveniently be observed by monitoring the temperature gradient along the body in the direction of flow of the heat current. It should be noted that the two scattering processes involved in the frequency crossing may be associated with scattering centres of the same type, or respectively with scattering centres of two different types.

While valuable results can be obtained with such known methods, their range of application is severely limited by the necessity for all the relevant scattering centres to be incorporated in a single body; this is particularly inhibiting in cases where it would be desirable to investigate the properties of a specific type of scattering centre in a specific host material by reference to the known properties of a different type of scattering centre. It is accordingly an object of the present invention to provide a method employing similar principles but of considerably enhanced versatility.

A method according to the invention comprises passing a heat current of phonons of broad spectral width through a composite solid structure incorporating two solid bodies respectively containing resonant phonon-scattering centres of different types, said bodies being so arranged that the occurrence of a frequency crossing involving two scattering processes respectively associated with said different types of centre will give rise to an excursion in the temperature difference between a pair of given locations on said structure spaced apart in the direction of flow of the heat current, subjecting said structure to a varying external perturbation so as to affect the resonant frequency of only one of said scattering processes, and monitoring the changes of said temperature difference caused by the variation of said perturbation.

Figure 2:
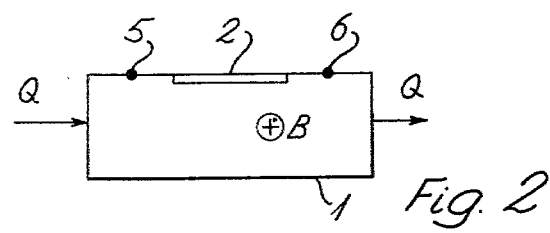
Figure 3:
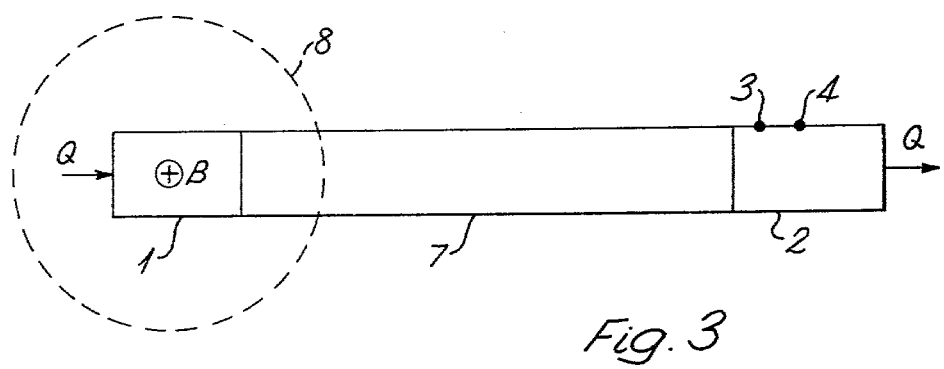

The invention will be further described and explained with reference to the accompanying drawings, in which FIGS. 1 to 3 are diagrammatic illustrations of three arrangements that may be used in methods according to the invention.

In each of these arrangements a heat current is arranged to pass from a heater to a heat sink constituted by a bath of liquid helium, through a composite solid structure incorporating a monocrystalline body of alumina doped with vanadium at a concentration of about 100 p.p.m. and a sample of a dielectric material containing resonant phonon-scattering centres which are to be investigated, the structure being maintained at a constant mean temperature of a few °K. by means of a suitable cryostat. The heater is constituted by a film or wire of a normal metal which is maintained in contact with an appropriate part of the composite structure and through which is passed a constant electric current. The heat current consequently consists of phonons whose frequency spectrum is similar to that of a black body radiator and has a width of several tens of GHz.

The arrangements illustrated in FIGS. 1 and 2 are suitable for the investigation of non-magnetic scattering centres in the sample, for example molecular defects with motional levels and possibly chain motion in polymers. In these arrangements the composite structure effectively consists of only the alumina crystal 1 and the sample 2, and is subjected to a magnetic field B directed perpendicular to the general direction of flow of the heat current Q, the crystal 1 being oriented so that its c-axis is parallel to the magnetic field B.

In the FIG. 1 arrangement, the sample 2 is in the form of a self-supporting body and the whole heat current Q is arranged to flow in succession through the crystal 1 and the sample 2. In the crystal 1 strong scattering will occur of phonons whose frequency corresponds to that of the sharp $\Delta M = 2$ transition of trivalent vanadium ions, so that the phonon current passing into the sample 2 is 'labelled' by an absorption line at this frequency, whose value is proportional to the magnetic flux density (with a numerical relationship of approximately 80 GHz/tesla). In carrying out an investigation with the FIG. 1 arrangement, the temperature difference between two points 3 and 4, spaced apart on the sample 2 in the direction of flow of the heat current Q, is continuously monitored while the frequency of the absorption line referred to above is swept through an appropriate range of values by variation of the magnetic field B. The consequent variation of the temperature difference will exhibit a minimum whenever the frequency of the absorption line referred to above is brought into coincidence with the frequency of an absorption line due to resonant phonon-scattering centres in the sample 2.

In certain cases it may be convenient to modify the arrangement shown in FIG. 1 by reversing the order of the crystal 1 and sample 2 in the heat current path. In such cases, it is of course necessary for the monitored temperature difference to be that between two points on the crystal 1 instead of on the sample 2.

In the FIG. 2 arrangement the crystal 1 is of generally cylindrical shape and the heat current Q is arranged to flow through it from end to end. The sample 2 is in the form of a film deposited in a groove cut in the crystal 1 so as to extend perpendicular to the cylindrical axis, the base of the groove being planar and being highly polished. As with the FIG. 1 arrangement, there will be strong scattering of the phonons by the trivalent vanadium ions in the crystal 1; there will also be significant scattering of the phonons at the interface between the crystal 1 and the sample 2, and the reflectivity at this interface will be substantially affected if there is a coincidence between the frequency of the absorption line due to the vanadium ions and the frequency of an absorption line due to resonant phonon-scattering centres in the sample 2. In this case, therefore, in carrying out an investigation the temperature difference between two points 5 and 6, located on the crystal 1 on either side of the sample 2, is continuously monitored while the frequency of the absorption line due to the vanadium ions is appropriately swept by variation of the magnetic field B.

FIG. 3 illustrates a variation of the FIG. 1 arrangement which may be adopted where it is desired to investigate magnetic phonon-scattering centres in the sample, for example donors or acceptors in a semiconductor. In this case the composite structure includes a further body 7 constituting a 'phonon guide', interposed between the crystal 1 and the sample 2; the body 7 may for example be a rod of very pure silicon having a highly polished surface. The magnetic field B in this case is confined to a limited region, indicated by the line 8; the crystal 1 is located within this region but the sample 2 is located outside it, so that the properties of the centres under investigation will not be affected by the presence of the magnetic field. With the FIG. 3 arrangement, an investigation is carried out in the same way as for the FIG. 1 arrangement.

In both the FIG. 1 and FIG. 3 arrangements, the individual bodies constituting the composite structure may in some cases be held together simply by mechanical pressure, but in other cases it may be desirable for these bodies to be bonded together. It appears desirable to avoid the use for this purpose of conventional glues, which are amorphous and contain tunnelling defects which are strongly coupled to phonons; it is thought that such defects would absorb the phonons and re-emit the 'labelled' spectrum as a black body spectrum. Accordingly it is considered preferable to use crystalline glues if it is required to bond the individual bodies together.

With all these arrangements, the monitoring of the relevant temperature difference may conveniently be effected by utilising a pair of thermometers of the semiconductor resistance type respectively located at the appropriate points, these thermometers being connected in a bridge circuit energised from an a.c. source (suitably having a frequency of about one kHz) and the out-of-balance signal from the bridge circuit being detected by means of a phase-sensitive detector to which a control signal is fed from the a.c. source. If desired, the signal/noise ratio for a given experiment can be improved by the employment of conventional signal averaging techniques involving a series of sweeps of the magnetic field. Sensitivity can also be improved by employing a differential technique involving modulation of the magnetic field as it is swept (the modulation suitably being at a frequency of a few Hz); in this case the output of the detector referred to above is fed to a second phase-sensitive detector supplied with a control signal corresponding to the field modulation. The resultant output is of a form which enables frequency crossing effects to be more readily distinguished from background effects.

It will be appreciated that the use in the illustrated arrangements of an alumina crystal doped with vanadium is referred to merely by way of example, and that in alternative embodiments of the invention there could be employed other types of body containing resonant phonon-scattering centres whose resonant frequency can be varied by the application of an external perturbation; as is the case with the known methods referred to above, this perturbation could be an electric field or a mechanical stress instead of a magnetic field.

I claim:

1. A method of phonon spectroscopy comprising:
   passing a heat current of phonons of broad spectral width through a composite solid structure incorporating two solid bodies respectively containing resonant phonons-scattering centres of different types, said bodies being so arranged that the occurrence of a frequency crossing involving two scattering processes respectively associated with said different types of centre will give rise to an excursion in the temperature difference between a pair of given locations on said structure spaced apart in the direction of flow of said heat current;
   subjecting said structure to a varying external perturbation so as to affect the resonant frequency of only one of said scattering processes; and
   monitoring the changes of said temperature difference caused by the variation of said perturbation.

2. A method according to claim 1, in which the whole of said heat current flows in succession through said two bodies, said given locations being disposed on the second of said two bodies in the direction of flow of said heat current.

3. A method according to claim 2, in which said external perturbation is a magnetic field.

4. A method according to claim 3, in which both of said two bodies are subjected to said magnetic field, said different types of scattering centre being respectively magnetic and non-magnetic.

5. A method according to claim 4, in which the magnetic scattering centres are trivalent vanadium ions incorporated in a monocrystalline body of alumina.

6. A method according to claim 3, in which said different types of scattering centre are both magnetic and only one of said two bodies is subjected to said magnetic field, said two bodies having interposed between them a third solid body constituting part of said composite structure and serving as a phonon guide.

7. A method according to claim 6, in which said third body is a rod of pure silicon having a polished surface.

8. A method according to either claim 6 or claim 7, in which that one of said two bodies which is subjected to said magnetic field is a monocrystalline body of alumina containing trivalent vanadium ions.

9. A method according to claim 2, in which the bodies constituting said composite structure are bonded together by means of crystalline glues.

10. A method according to claim 1, in which one of said two bodies is elongated and has formed in it a groove extending transversely to its length, the other of said two bodies being constituted by a film deposited in said groove, said heat current flowing through said one of said two bodies from end to end, and said given locations being disposed on said one of said two bodies respectively on either side of said groove.

11. A method according to claim 10, in which said external perturbation is a magnetic field, the types of scattering centre contained in said one and said other of said two bodies respectively being magnetic and non-magnetic.

12. A method according to claim 11, in which said one of said two bodies is a monocrystalline body of alumina containing trivalent vanadium ions.

* * * * *